US00PP32949P2

(12) United States Plant Patent
Walker et al.

(10) Patent No.: US PP32,949 P2
(45) Date of Patent: Apr. 6, 2021

(54) GRAPEVINE PLANT NAMED 'AMBULO BLANC'

(50) Latin Name: ***Vitis vinifera* L.**
Varietal Denomination: Ambulo Blanc

(71) Applicant: The Regents of the University of California, Oakland, CA (US)

(72) Inventors: Michael Andrew Walker, Davis, CA (US); Alan C. Tenscher, Davis, CA (US); Summaira Riaz, Davis, CA (US); Ninfa Romero, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/602,591

(22) Filed: Nov. 5, 2019

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206, 295
See application file for complete search history.

(56) References Cited

PUBLICATIONS

The Apr. 1, 2014 Test Agreement For Grape vines (No. 2015-5011) between Silverado Vineyards and The Regents of the University of California, 7 pages.
The May 1, 2014 Test Agreement For Grape vines (No. 2016-5008) between Ben R. Drake Enterprises, Inc. and The Regents of the University of California, 7 pages.
The May 16, 2017 Test Agreement For Grapevines (No. 2017-5008) between Wonderful Nurseries, LLC and The Regents of the University of California, 7 pages.
The May 17, 2017 Test Agreement For Grapevines (No. 2017-5011) between Sunridge Nurseries, Inc. and The Regents of the University of California, 6 pages.
The May 18, 2017 Test Agreement For Grapevines (No. 2017-5009) between Novavine and The Regents of the University of California, 6 pages.
The May 24, 2017 Test Agreement For Grapevines (No. 2017-5010) between Sutter Home Winery, Inc. and The Regents of the University of California, 7 pages.

*Primary Examiner* — Susan McCormick Ewoldt
(74) *Attorney, Agent, or Firm* — McKee, Voorhees & Sease, PLC

(57) ABSTRACT

A new and distinct variety of grapevine plant named 'Ambulo Blanc', particularly selected for its high resistance to Pierce's disease, as well as quality of fruit and wines produced is disclosed.

6 Drawing Sheets

Botanical classification: *Vitis vinifera* L.

Varietal denomination: The varietal denomination of the claimed variety of grapevine plant is 'Ambulo Blanc'.

BACKGROUND OF THE INVENTION

Pierce's disease (PD) is common across the southern United States from Virginia to northern California. It is also common across Mexico and Central America. The disease is caused by the bacterium *Xylella fastidiosa*, which is hosted by a very wide range of native and ornamental plants. The bacterium is spread by xylem feeding insects as vectors, primarily sharpshooters. PD is one of the few diseases that rapidly kills wine, table, and raisin grape cultivars of the cultivated grape, *Vitis vinifera*. Vector populations can be limited with insecticides, but these are difficult to use near their typically riparian native habitat or in the ornamental landscapes in which they flourish. Breeding for PD resistance has been active for over 70 years, but progress has been very slow due to a poor understanding of the germplasm and the typically multigenic nature of the resistance in most of the resistant grape species. The two most commonly grown PD resistant varieties, 'Blanc du Bois' and 'Lenoir' ('Lenoir' is also known as 'Black Spanish' or 'Jacquet'), are $F_1$ hybrids between *V. vinifera* cultivars and resistant American grape species from the southern United States, and are therefore only about 50% of *V. vinifera*. 'Blanc du Bois' and 'Lenoir' produce wines with lower quality than *V. vinifera* wine grape varieties, and they are tolerant of, rather than resistant to, *X. fastidiosa* infection, which results in their potential to expand areas damaged by PD due to their ability to act as host plants for the bacteria and vectors.

Grapevine is an important and valuable crop. Accordingly, there is a need for new varieties of grapevine plant. In particular, there is a need for improved varieties of grapevine plant that produce high quality fruit for winemaking and are resistant to Pierce's disease.

SUMMARY OF THE INVENTION

In order to meet these needs, the present invention is directed to an improved variety of grapevine plant. In particular, the invention relates to a new and distinct variety of grapevine plant (*Vitis vinifera* L.), which has been denominated as 'Ambulo Blanc'. Grapevine plant variety 'Ambulo Blanc' possesses very strong resistance to the bacterial causal agent of Pierce's disease (PD), and produces very high quality fruit and wines therefrom that are indistinguishable from the widely grown European wine grape cultivars. Other PD resistant cultivars are known, but their fruit and winemaking quality are poor in comparison to 'Ambulo Blanc' and their resistance is much lower.

In particular, grapevine plant variety 'Ambulo Blanc' is a white wine grape selection that is about 97% *V. vinifera* (including 62.5% 'Cabernet Sauvignon', 12.5% 'Carignane', and 12.5% 'Chardonnay') and is highly resistant to PD as shown in repeated greenhouse evaluations. In comparison, the two most commonly grown PD resistant varieties, 'Blanc du Bois' and 'Lenoir', are only about 50% of *V. vinifera*. 'Ambulo Blanc' has been tested in Ojai, Sonoma, and along the Napa River in California. 'Ambulo Blanc' has an early bloom and its fruit ripen early. It has small to medium berries and relatively large clusters, and is highly productive. Wines made from fruit of 'Ambulo Blanc' are reminiscent of 'Sauvignon Blanc' and may be described as: 'light straw to clear color', 'citrus', 'lime', 'tropical', 'gooseberry and golden delicious apple flavors', 'bright fruit', 'slightly bitter', and 'textured'.

Pedigree and Breeding History

The development of this new grapevine variety is in part a result of the discovery of a single dominant gene for resistance to *Xylella fastidiosa*, the bacterial causal agent of Pierce's disease (PD). The source of the PD resistance is a form of *V. arizonica* ('b43-17') that appears to have some candicans parentage and is from Monterrey, Mexico. 'b43-17' was crossed to the susceptible *V. rupestris* 'A. de Serres' to create the F8909 population. Neither 'b43-17' nor 'A. de Serres' are patented. The resistance from 'b43-17' was found to be inherited as a single dominant gene (locus), and this resistance gene, PdRl, was genetically mapped using the F8909 population by a grapevine breeding program. Tightly linked simple sequence repeat (SSR) markers were developed and were used in marker-assisted selection to exclude susceptible plants from evaluation in each round of selection. All the progeny with PdRl were tested for PD resistance and only those with strong resistance were considered for use as parents. Potential parents were also screened for fruit quality over generations and only those with good quality fruit and that appeared like *V. vinifera* were selected.

Line 'F8909-08' from the F8909 population was crossed to 'P79-101', a highly susceptible, advanced *V. vinifera* table grape selection a grape breeding program. The resulting 'F8909-08' X 'P79-101' $F_1$ generation and progeny thereof were screened with the SSR markers for resistance to *X. fastidiosa* under greenhouse conditions. A highly resistant selection from the 'F8909-08' X 'P79-101' cross, '00504-20', was crossed to another *V. vinifera* table grape from a grape breeding program, 'B52-89', to create 'A81-138', which was also selected for its very high resistance to PD. 'A81-138' was then used to cross to *V. vinifera* wine grapes for several generations of modified backcrossing to obtain the candidate selection '09314-102', which was later named as 'Ambulo Blanc'. These backcrosses were modified because of the high heterozygosity and recessive load found in grapes. Hence, to avoid exposure of deleterious recessive alleles, each generation of backcrossing was to a different and unrelated high quality *V. vinifera* cultivar.

Accordingly, the parentage of 'Ambulo Blanc' is '07370-028' (*V. vinifera* 'F2-35' ('Cabernet Sauvignon' X 'Carignane') X 'U0502-38' ('A81-138' X *V. vinifera* 'Chardonnay')). '07370-028' was crossed with *V. vinifera* 'Cabernet Sauvignon' to produce '09314-102' and this selection was later named 'Ambulo Blanc'. 'Ambulo Blanc' was particularly selected for its high resistance to Pierce's disease, as well as the quality of its fruit and wines produced therefrom. '09314-102' is a cross between '07370-28' X 'Cabernet Sauvignon'. '07370-28' is highly resistant to *X. fastidiosa* has lobed leaves. 'Cabernet Sauvignon' is not only very susceptible to *X. fastidiosa*, it has deeply lobed leaves with relatively short teeth on the leaf margin, has short sinuses on the lateral lobes and is a red wine grape. None of the parents across the multiple backcross generations are patented. 'Ambulo Blanc' can be distinguished from its male parent 'Cabernet Sauvignon' by its high resistance to *X. fastidiosa*. 'Ambulo Blanc' can be distinguished from its female parent '07370-028' in that 'Ambulo Blanc' has perfect flowers whereas '07370-028' has pistillate flowers.

BRIEF DESCRIPTION OF THE DRAWINGS

This new grapevine plant variety is illustrated by the accompanying photographs. The colors shown are as true as can be reasonably obtained by conventional photographic procedures. The photographs are of plants that are five to seven years old. Colors referred to are in reference to The Royal Horticultural Society Colour Charts Edition V.

FIG. 1 shows simple sequence repeat (SSR) marker data establishing a DNA fingerprint for 'Ambulo Blanc' with nine pure *Vitis vinifera* cultivars for comparison. Alleles for marker-assisted selection of the *Xylella fastidiosa* locus (PdRl) are shown in red.

DETAILED BOTANICAL DESCRIPTION

The following is a detailed description of the new grapevine plant variety designated as 'Ambulo Blanc', including the key differentiating characteristics of this variety and comparisons of characteristics of 'Ambulo Blanc' to other grapevine varieties. Unless otherwise indicated, evaluation data were taken from five- to seven-year-old plants, grown in Davis, Calif.

Classification:

*Family*.—Vitaceae.

*Botanical name*.—*Vitis vinifera* L.

*Common name*.—Grapevine.

*Variety name*.—'Ambulo Blanc'.

Parentage:

*Female parent*.—'07370-028' (unpatented).

*Male parent*.—'Cabernet Sauvignon' (unpatented) Note that 'Cabernet Sauvignon' is a hermaphroditic cultivar and thus can be used as a maternal or paternal parent.

Plant:

*Berries*.—Small to medium, spherical, green to yellow green, thin green/white bloom.

*Clusters*.—Medium to large, long conical, compact to well-filled.

*Leaves*.—Five-lobed, overlapping lobes with occasional teeth in the sinus, overlapping circular petiolar sinus, relatively short 2-ranked teeth on leaf margin, glabrous adaxial surface, short sparse tomentum on the abaxial surface, brown-red petioles, and color diffuses into the veins.

*Shoot tips*.—Erect green/white tomentum.

*Production*.—Early bloom and ripens early, highly productive.

*Method of propagation*.—Vegetative propagation via woody or herbaceous cuttings, or budding and grafting to rootstock. 'Ambulo Blanc' has been asexually reproduced in Davis, Calif. Any rootstock can be used with the variety. Most often it will be grown on rootstocks that resist grape phylloxera and or nematodes. In testing, selections were evaluated grafted on '1103P' rootstock which is not patented. It was chosen for ease of propagation and because it is widely used in CA. The variety has been grafted on many other rootstocks for testing in field trials as well.

'Ambulo Blanc' has the highest form of resistance to *X. fastidiosa* coupled with the highest wine quality of any PD resistant wine grape yet produced. 'Ambulo Blanc' is selected for very high resistance, not the more commonly found tolerance, to prevent the production of host plants capable of further spreading PD to surrounding vineyards.

'Ambulo Blanc' has a very strong PD resistance and the highest wine quality of any currently used PD resistant wine grape. PD is one of the few diseases that kill susceptible grapevines. Two most popular PD resistant wine grape varieties, 'Blanc du Bois' and 'Lenoir' ('Lenoir' is also known as 'Black Spanish' or 'Jacquez'), were used as controls or standards in all testing so that the wine quality and resistance of the candidate variety could be compared to available PD resistant varieties used across the southern United States. It is noted that 'Blanc du Bois' and 'Lenoir' have relatively poor wine quality and are tolerant, not resistant, to PD. Neither 'Blanc du Bois' nor 'Lenoir' are patented.

Figure 2:
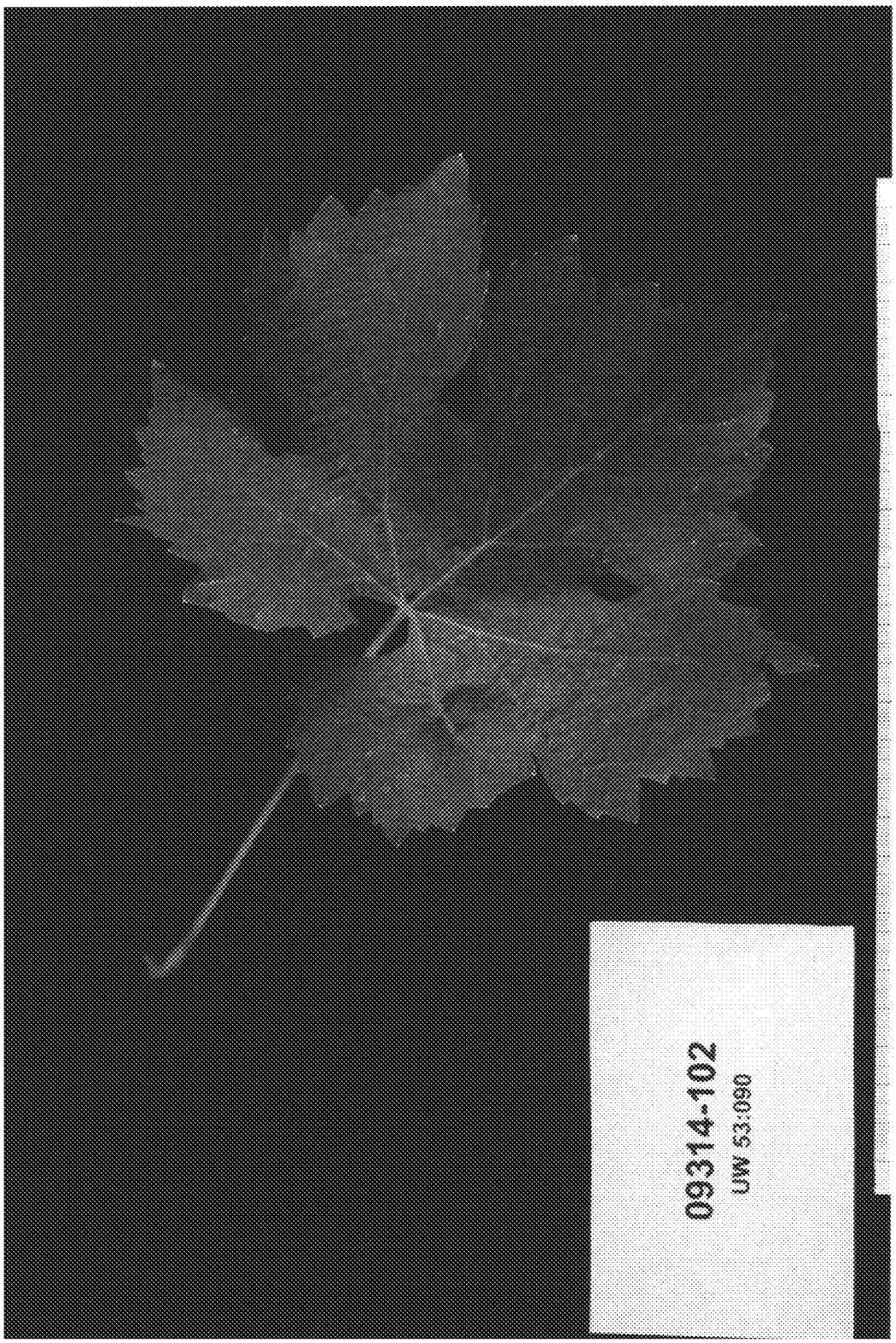
FIG. 2 illustrates the upper surface of a leaf of grapevine plant variety 'Ambulo Blanc'.
Figure 3:
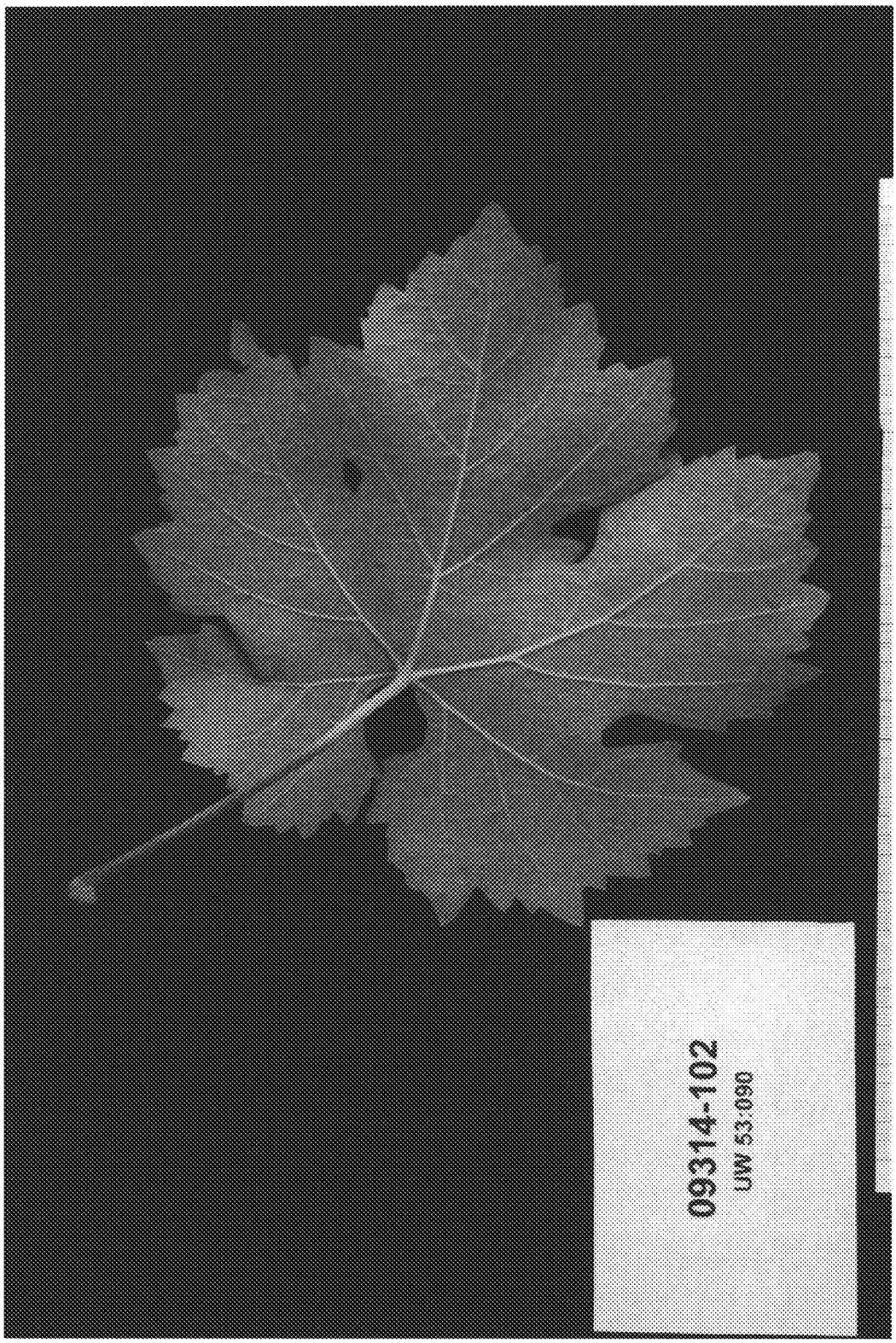
FIG. 3 illustrates the lower surface of a leaf of grapevine plant variety 'Ambulo Blanc'.
Figure 4:
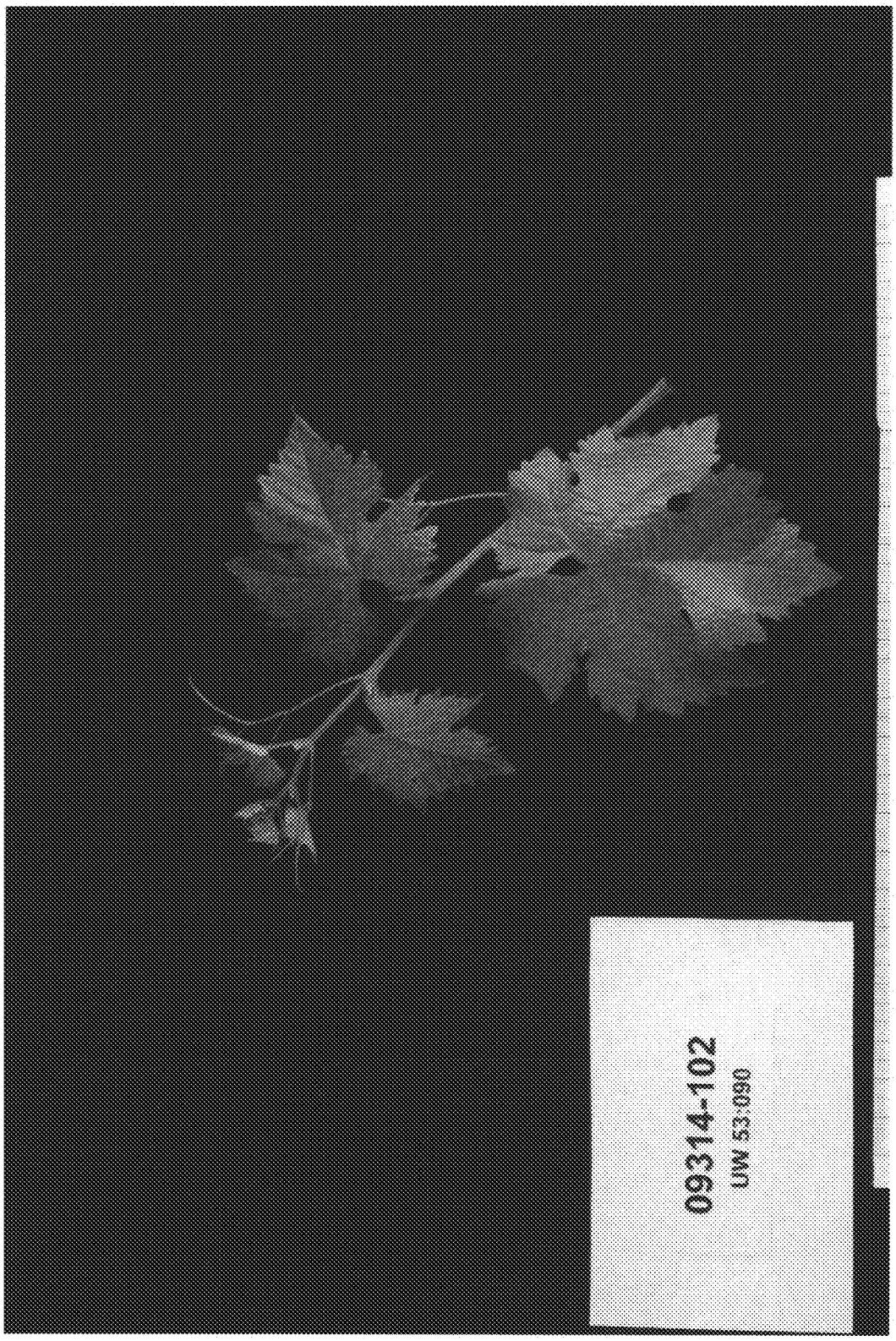
FIG. 4 illustrates a section of a shoot tip of grapevine plant variety 'Ambulo Blanc'.
Figure 5:
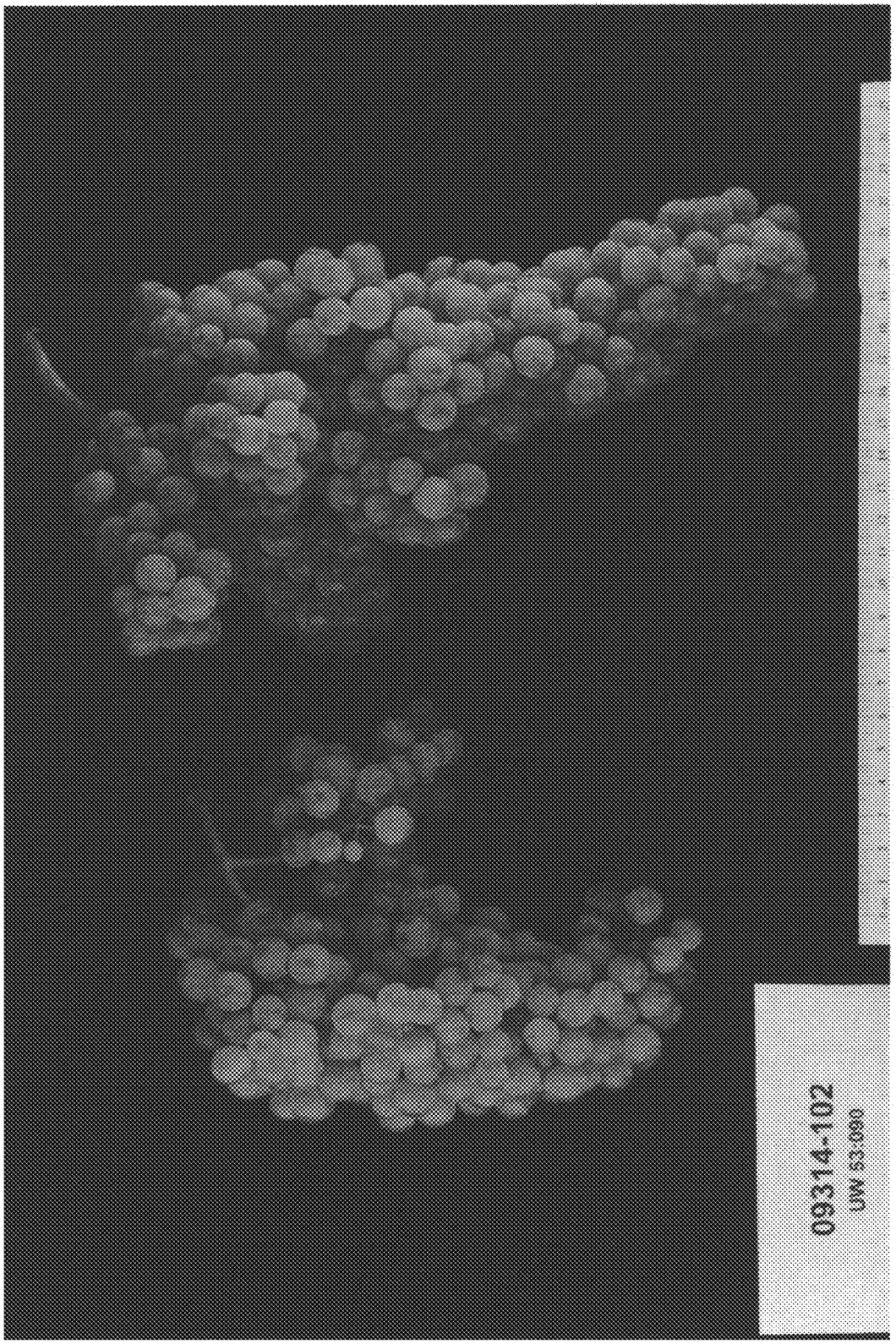
FIG. 5 illustrates clusters of berries of grapevine plant variety 'Ambulo Blanc'.
Figure 6:
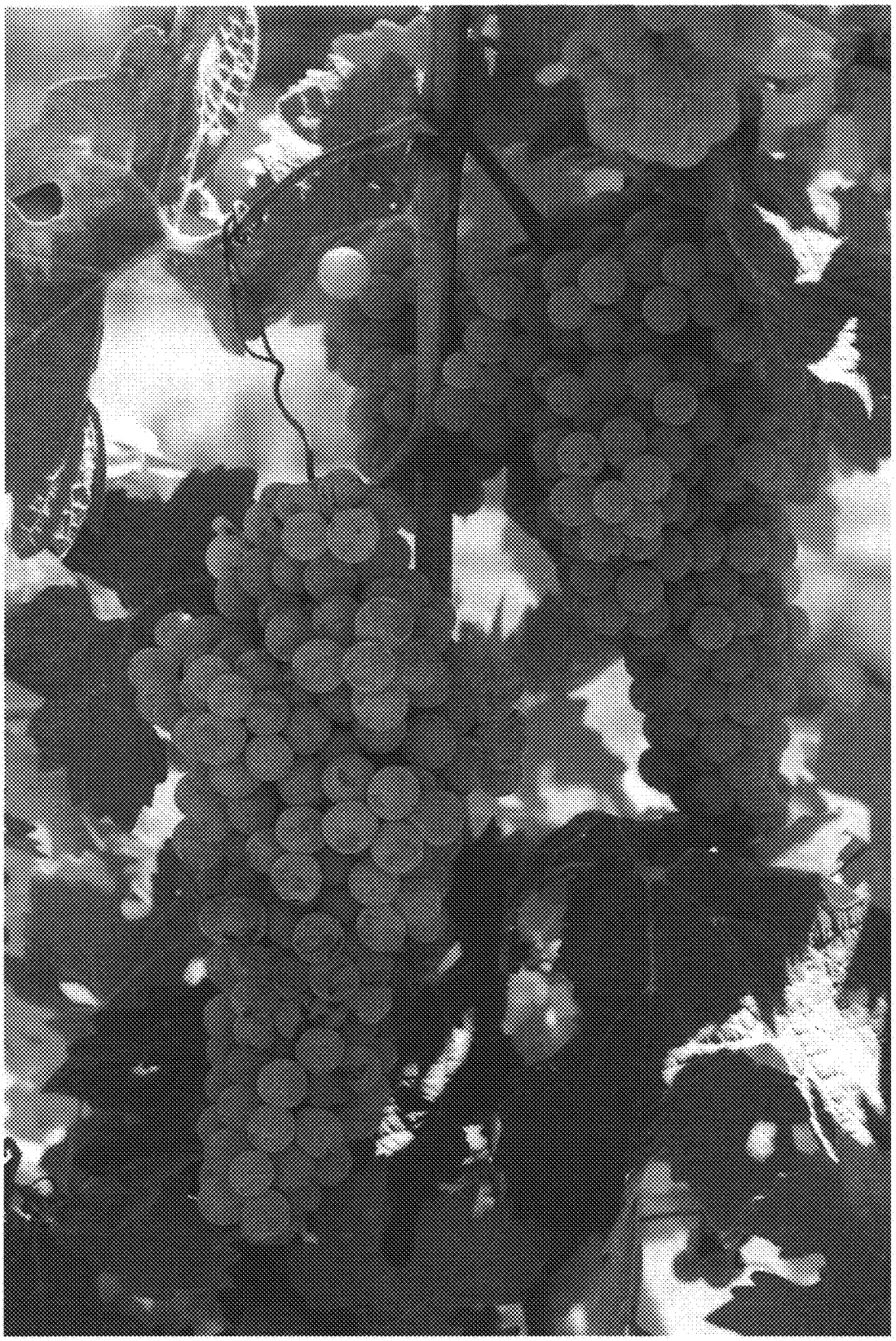
FIG. 6 illustrates a plant of grapevine plant variety 'Ambulo Blanc'.

'Ambulo Blanc' has far better PD resistance and wine quality when compared with 'Blanc du Bois' and 'Lenoir'. In other words, 'Ambulo Blanc' combines very strong resistance to *X. fastidiosa* with the wine quality of internationally acclaimed wine grape cultivars. 'Ambulo Blanc' was selected as a variety that exhibits high resistance to *X. fastidiosa* and *V. vinifera*-like wine quality. The data presented below are intended to further characterize 'Ambulo Blanc'. The appearance of 'Ambulo Blanc' is illustrated in FIGS. 2-6, and further characteristics of 'Ambulo Blanc' are shown in Tables 1-5.

FIG. 1 presents the DNA fingerprinting profile for 'Ambulo Blanc' and nine pure *Vitis vinifera* cultivars for comparison with the standard set of internationally agreed-upon genetic markers. This SSR fingerprinting profile can be used for DNA-based identification.

Table 1 presents typical phenological data for 'Ambulo Blanc' grown in vineyards. These data are for 2016, but the ranking of the selections in regard to an early cultivar ('Pinot noir') and a late cultivar ('Cabernet Sauvignon') have been typical over years. In general, 'Ambulo Blanc' is phenologically mid-season. Based upon the percentage of *V. vinifera* in the present variety and the data regarding its parents, the variety is expected to grow in USDA Hardiness Zone 6-7. It is not expected to be drought tolerant.

TABLE 1

Average phenological states for 'Ambulo Blanc'. 'Cabernet Sauvignon' (late) and 'Pinot noir' (early) are included as comparisons. All data were taken from vineyards.

| Cultivar | Budbreak | 50% bloom | 50% veraison | 24 °Brix |
|---|---|---|---|---|
| 'Ambulo Blanc' | 3/17 | 5/1 | 7/17 | 8/16 |
| 'Cabernet Sauvignon' | 3/24 | 5/7 | 7/21 | 8/30 |
| 'Pinot Noir' | 3/10 | 4/30 | 7/9 | 8/9 |

Table 2 presents the average cluster and berry data for 'Ambulo Blanc' and averaged over multiple years.

TABLE 2

Average cluster and berry sizes of 'Ambulo Blanc' and its comparison varieties. Data are averages over multiple years.

| Genotype | Number of Years | Avg. Cluster Wt. (g) | t-test Cluster Wt. | Avg. Berry Wt. (g) | t-test Berry Wt | Clusters |
|---|---|---|---|---|---|---|
| 'Ambulo Blanc' | 6 | 340 | a | 1.3 | bc | Well-filled to compact |
| 'Blanc du Bois' | 6 | 148 | d | 1.5 | a | Well-filled |
| 'Cabernet Sauvignon' | 6 | 132 | d | 1.2 | c | Loose to well-filled |
| 'Chardonnay' | 6 | 196 | cd | 1.5 | ab | Well-filled to compact |
| 'Lenoir' | 6 | 157 | d | 1.3 | bc | Loose |

Table 3 presents the average yield per vine data taken over 2016 to 2018.

TABLE 3

Average production data for 'Ambulo Blanc' and its comparison varieties. Data are averages from three years (2016 to 2018).

| Genotype | Avg. Yield/ Vine (kg) | Std. Dev. (kg) | t-test | Number of Years |
|---|---|---|---|---|
| 'Ambulo Blanc' | 11.4 | 3.6 | a | 3 |
| 'Blanc du Bois' | 12.7 | 1.8 | a | 3 |
| 'Cabernet Sauvignon' | 10.9 | 1.8 | a | 3 |
| 'Chardonnay' | 10.9 | 3.2 | a | 3 |
| 'Lenoir' | 20.0 | 6.8 | b | 3 |

Mean berry juice data were also taken and Table 4 presents this data over a five-year period between 2014 and 2018. These values are consistent with cultivars that produce high quality wines.

TABLE 4

Average juice data for 'Ambulo Blanc' and its comparison varieties. Data are averages from five years (2014 to 2018).

| Genotype | Avg. ° Brix | t-test Avg. ° Brix | Avg. pH | t-test Avg. pH |
|---|---|---|---|---|
| 'Ambulo Blanc' | 23.7 | c | 3.66 | bc |
| 'Blanc du Bois' | 23.5 | c | 3.58 | bc |
| 'Cabernet Sauvignon' | 25.8 | b | 3.74 | abc |

TABLE 4-continued

Average juice data for 'Ambulo Blanc' and its comparison varieties. Data are averages from five years (2014 to 2018).

| | | | | |
|---|---|---|---|---|
| 'Chardonnay' | 23.3 | cd | 3.68 | bc |
| 'Lenoir' | 21.3 | e | 3.96 | a |

| Genotype | Avg. titratable acidity (g/L) | t-test Avg. TA | Avg. L-malic acid (g/L) | t-test Avg. MA |
|---|---|---|---|---|
| 'Ambulo Blanc' | 7.0 | b | 4.5 | a |
| 'Blanc du Bois' | 5.2 | de | 2.3 | bcd |
| 'Cabernet Sauvignon' | 5.2 | de | 1.9 | bcd |
| 'Chardonnay' | 5.9 | cd | 2.4 | bc |
| 'Lenoir' | 9.1 | a | 4.5 | a |

*Xylella fastidiosa* susceptibility data are presented in Table 5, which presents the levels of *X. fastidiosa* in relationship to tolerant ('Blanc du Bois' and to a lesser extent, 'Lenoir') and susceptible ('Chardonnay' and 'Cabernet Sauvignon') cultivars. These are also mean data from repeated testing over seasons and greenhouses. Because of the high variation in greenhouse conditions, at least four standards (bio-controls) were always used: 'b43-17', 'Blanc du Bois', 'Lenoir', and 'Chardonnay' (and occasionally other *V. vinifera* cultivars), which allows the data to be compared across greenhouses, tests and seasons. None of these varieties are patented. These varieties tend to be very consistent in the amounts of bacteria they support as well as the severity of their disease expression. The cut-off between resistant and susceptible is usually between 75,000 and 250,000 colony forming units per milliliter (cfu/ml).

TABLE 5

*Xylella fastidiosa* concentrations based on ELISA readings and converted to colony forming units (cfu/ml). *Vitis arizonica* 'b43-17' is the source of resistance in the breeding program.

| Cultivar | Geometric Mean cfu/ml | t-test | Least Sq. Mean | Std. Error | Number of Times Tested |
|---|---|---|---|---|---|
| 'b43-17' | 12423 | a | 9.4 | 0.2 | 11 |
| 'Ambulo Blanc' | 102893 | b | 11.5 | 0.3 | 5 |
| 'Blanc du Bois' | 859096 | c | 13.7 | 0.2 | 11 |
| 'Lenoir' | 2421748 | d | 14.7 | 0.6 | 2 |
| 'Chardonnay' | 5197228 | d | 15.5 | 0.2 | 11 |
| 'Cabernet Sauvignon' | 6582993 | d | 15.7 | 0.8 | 1 |

TABLE 6 shows phenotype of 'Ambulo Blanc'. The variety has normal hermaphroditic flowers and typical floral development as is found in commercial *V. vinifera* wine grapes.

| | 'Ambulo Blanc' |
|---|---|
| Berry size (L, W) | 1.4 × 1.3 cm |
| Berry weight, shape | 1.0 g/round |
| On average, two seeds per berry. Seed number, length and width typical for *V. vinifera* wine grapes, but not measured | 2 |

TABLE 6-continued shows phenotype of 'Ambulo Blanc'. The variety has normal hermaphroditic flowers and typical floral development as is found in commercial *V. vinifera* wine grapes.

| | 'Ambulo Blanc' |
|---|---|
| Cluster #, L, W, shape, compactness, 2 clusters/shoot | 11.0 × 27.0 cm, long cylindrical single to winged, well-filled to compact |
| Yield kg | 15.6 |
| Pruning weights | 2.8 kg |
| Trunk width at 30 cm | 3.8 cm |
| Trunk color and texture | Rough shaggy bark 178D |
| Woody shoots diameter above cluster/ and internode length | 0.9 cm/5.3 cm |
| Woody shoot texture and color | First year bark adheres but peels in strips in second year 164B |
| Active shoot color, internode color above the cluster zone/ cluster zone shoot diameter/internode length (shoots same size as woody canes in the cluster zone) | 142C 144C 0.9/5.3 cm |
| Tendril length, diameter | 8.0 0.1 |
| Tendril color, Opposite leaves and alternating 2 nodes skip 2 nodes skip | N144C |
| Seed color | 165B |
| Cluster size L, W | 11.0 × 27.0 cm |
| #Berries/cluster | 452 |
| Berry color skin and waxy bloom | 144A 190D |
| Berry flesh color | 144A |
| Leaves L, W | 21.0 × 23.0 |
| Leaf arrangement, shape, and color Top/Bottom | Alternate, palmate with 5 lobes 143A/142B |
| Petiole L, diameter, texture | 14.0 0.4 smooth |
| Petiole color | N77B |
| Shoot tip color (first opened leaf) | 144D |
| Budbreak | Mar. 15 |
| Bloom date | May 15 |
| Harvest date | Aug. 13 |
| Peduncle L, diam., color, texture | 5.5 0.7 144B Smooth |

Flower Descriptions

The floral buds and flower clusters are formed with in the latent (dormant) bud in the year before flowering. As the pre-formed nodes on the compressed stems within the latent bud expand and the flower clusters begin developing and the individual flowers on the panicle begin forming. They are very small 2-4 mm and closer to 2 mm with wine grapes.

Berry Descriptions

The variety is not a "slip-skin" type grape. They have skin that adheres to the flesh tightly. They are not firm at ripeness and are soft compared to modern era table grapes at harvest. The pedicels have normal attachment to the berries and are not distinguishable from other *V. vinifera* wine grapes in this or other morphological features, nor in juice and wine analysis.

Leaf Descriptions

Rounded leaves with overlapping relatively shallow lateral sinuses, circular overlapping petiolar sinus, short sharp teeth, light tomentum, petioles with light red (N77B) color with limited diffusion into the main veins

Fruit and Juice Parameters

YAN is yeast assimilable nitrogen and helps predict fermentation success. The white grapes have no tannin or anthocyanin values. Seed color is rated as green to brown for mature seeds.

TABLE 7 presents the wine characteristics of 'Ambulo Blanc'

| | ° Brix | TA (g/L) | pH | L-malic acid (g/L) | Potassium (mg/L ) | YAN (mg/L, as N) |
|---|---|---|---|---|---|---|
| 'Ambulo Blanc' | 24.2 | 6.4 | 3.64 | 3.6 | 2160 | 223 |

TABLE 8 presents the juice, fruit and seed phenotype of 'Ambulo Blanc'

| | Juice Hue | Juice Intensity | Juice Flavor | Skin Flavor |
|---|---|---|---|---|
| 'Ambulo Blanc' | green-yellow | Lt Light | pear, sl spice | neutral, fruity, sl veg |
| | Skin Tannin (1 = low, 4 = high) | Seed Color (1 = gr, 4 = br) | Seed Flavor | Seed Tannin (1 = high, 4 = low) |
| 'Ambulo Blanc' | 1 | 4 | buttery, sl woody | 4 |

'Ambulo Blanc' has excellent PD resistance. However, it is highly susceptible to a wide range of pests and diseases in a manner similar to other *V. vinifera* cultivars, and thus it must be treated as a pure *V. vinifera* cultivar in terms of susceptibility to fungal diseases and pests. 'Ambulo Blanc' has no known tolerance to adverse weather.

What is claimed is:

1. A new and distinct variety of grapevine plant designated 'Ambulo Blanc' as shown and described herein.

* * * * *

| Marker Alleles for the International Set of SSR Loci for Fingerprinting Grape | | | | | | | | | | | | | | | | | | | | |
|---|---|---|---|---|---|---|---|---|---|---|---|---|---|---|---|---|---|---|---|---|
| Cultivar | VVMD5 | | VVMD7 | | VVS2 | | VrZAG79 | | VrZAG62 | | VVMD31 | | VVMD27 | | VVMD32 | | VVIP26 | | CH14-77 | |
| Ambulo Blanc | 226 | 229 | 235 | 235 | 134 | 146 | 242 | 242 | 184 | 190 | 202 | 206 | 183 | 183 | 237 | 253 | 146 | 160 | 178 | 202 |
| Riesling | 226 | 235 | 235 | 235 | 134 | 146 | 242 | 242 | 184 | 190 | 202 | 206 | 169 | 183 | 237 | 237 | 160 | 166 | 178 | 178 |
| Alicante Bouschet | 220 | 233 | 235 | 239 | 128 | 140 | 238 | 252 | 184 | 184 | 208 | 208 | 175 | 188 | 247 | 269 | 154 | 160 | 178 | 178 |
| Chenin blanc | 220 | 226 | 235 | 249 | 128 | 128 | 240 | 246 | 192 | 196 | 212 | 212 | 183 | 185 | | | 160 | 160 | 178 | 185 |
| Zinfandel | 220 | 230 | 243 | 245 | 128 | 138 | 232 | 254 | 196 | 200 | 208 | 210 | 173 | 175 | 253 | 261 | 160 | 160 | 178 | 178 |
| Touriga Nacional | 220 | 220 | 235 | 235 | 138 | 146 | 240 | 240 | 184 | 190 | 200 | 212 | 175 | 183 | 237 | 269 | 140 | 154 | 168 | 178 |
| Semillon | 233 | 235 | 235 | 245 | 132 | 138 | 234 | 238 | 190 | 200 | 210 | 212 | 175 | 179 | 237 | 247 | 154 | 160 | 178 | 178 |
| Palomino | 220 | 220 | 239 | 243 | 128 | 128 | 250 | 254 | | | 200 | 212 | 173 | 175 | 253 | 259 | 154 | 160 | 178 | 178 |
| Chardonnay | 229 | 233 | 235 | 239 | 132 | 138 | 238 | 240 | 184 | 192 | 210 | 212 | 175 | 183 | 237 | 269 | 154 | 180 | 178 | 178 |
| Cabernet Sauvignon | 226 | 235 | 235 | 235 | 134 | 146 | 242 | 242 | 184 | 190 | 202 | 206 | 169 | 183 | 237 | 237 | 160 | 166 | 178 | 178 |

FIG. 1